(12) United States Patent
Muser et al.

(10) Patent No.: US 11,395,690 B2
(45) Date of Patent: Jul. 26, 2022

(54) CANNULATED T-HANDLE DRIVER

(71) Applicant: CONMED CORPORATION, Utica, NY (US)

(72) Inventors: Andrew P. Muser, St. Pete Beach, FL (US); Andrew Kam, Odessa, FL (US)

(73) Assignee: CONMED CORPORATION, Utica, NY (US)

( * ) Notice: Subject to any disclaimer, the term of this patent is extended or adjusted under 35 U.S.C. 154(b) by 330 days.

(21) Appl. No.: 16/650,969

(22) PCT Filed: Aug. 29, 2018

(86) PCT No.: PCT/US2018/048434
§ 371 (c)(1),
(2) Date: Mar. 26, 2020

(87) PCT Pub. No.: WO2019/046359
PCT Pub. Date: Mar. 7, 2019

(65) Prior Publication Data
US 2020/0268427 A1 Aug. 27, 2020

Related U.S. Application Data

(60) Provisional application No. 62/552,460, filed on Aug. 31, 2017, provisional application No. 62/640,817, filed on Mar. 9, 2018.

(51) Int. Cl.
*A61B 17/88* (2006.01)
*A61B 17/86* (2006.01)
*A61B 17/00* (2006.01)

(52) U.S. Cl.
CPC ........ *A61B 17/8875* (2013.01); *A61B 17/864* (2013.01); *A61B 2017/0046* (2013.01)

(58) Field of Classification Search
CPC .......................... A61B 17/8875; A61B 17/864
See application file for complete search history.

(56) References Cited

U.S. PATENT DOCUMENTS

| | | | |
|---|---|---|---|
| 4,996,896 A | * | 3/1991 | Bachand ................ B25G 1/066 81/450 |
| 5,464,407 A | | 11/1995 | McGuire |

(Continued)

FOREIGN PATENT DOCUMENTS

| | | |
|---|---|---|
| CN | 203031521 | 7/2013 |
| CN | 203945305 | 11/2014 |
| WO | 2016/130794 | 8/2016 |

OTHER PUBLICATIONS

International Search Report Form PCT/ISA/220, International Application No. PCT/US2019/052546, pp. 1-15, dated Mar. 9, 2020.

*Primary Examiner* — Christian A Sevilla
(74) *Attorney, Agent, or Firm* — Bond, Schoeneck & King, PLLC; Frederick J.M. Price

(57) ABSTRACT

A driver assembly with a rotatable and interchangeable cannulated driver shaft for drilling a variety of fasteners. The driver assembly includes an elongated body having a proximal end and a distal end with a first channel extending from the distal end into the elongated body and a second channel extending from a first side of the elongated body into the elongated body. The driver assembly also includes a locking mechanism connected within the elongated body. The locking mechanism is rotatable between a first configuration and a second configuration. A cannulated driver shaft is removably attached to the locking mechanism and is rotatable between the first configuration and the second configuration via the locking mechanism.

20 Claims, 19 Drawing Sheets

(56) References Cited

U.S. PATENT DOCUMENTS

| | | | |
|---|---|---|---|
| 5,822,830 A * | 10/1998 | Lin | B25G 1/005 |
| | | | 81/177.1 |
| 7,226,456 B2 | 6/2007 | O'Neil et al. | |
| 7,287,450 B1 * | 10/2007 | Liao | B25B 15/02 |
| | | | 81/177.9 |
| 9,216,049 B2 | 12/2015 | Rabiner et al. | |
| 9,919,412 B2 * | 3/2018 | Petit | B25G 1/08 |
| 10,194,969 B2 | 2/2019 | Overes et al. | |
| 10,315,302 B2 * | 6/2019 | Lin | B25G 1/063 |
| 10,575,888 B2 | 3/2020 | Coillard-Lavirotte et al. | |
| 2004/0127888 A1 * | 7/2004 | O'Neil | A61B 17/8875 |
| | | | 606/1 |
| 2007/0227314 A1 * | 10/2007 | Erickson | A61B 17/862 |
| | | | 81/467 |
| 2016/0143682 A1 * | 5/2016 | Overes | A61B 17/8875 |
| | | | 606/104 |

\* cited by examiner

CANNULATED T-HANDLE DRIVER

CROSS-REFERENCE TO RELATED APPLICATIONS

This application claims priority to U.S. Provisional Patent Application Ser. No. 62/552,460, filed on Aug. 31, 2017 and entitled "Cannulated T-Handle Driver" and U.S. Provisional Patent Application Ser. No. 62/640,817, filed on Mar. 9, 2018 and entitled "Cannulated T-Handle Driver, Modulated."

BACKGROUND OF THE INVENTION

1. Field of the Invention

The invention relates generally to a driver for drilling screws at a surgical site and, more particularly, to a driver assembly with a rotatable and interchangeable cannulated driver shaft for drilling a variety of fasteners.

2. Description of Related Art

Screws are often used in orthopedic surgeries. A manual driver is frequently used to torque the screws to a specific position or depth at a surgical site. In a surgical environment, fluids can make gripping these drivers more difficult. This is especially true when saline, blood, and/or lipids are involved. When the conditions are such that gripping the driver is more difficult, there is less torque to drill the screws at the surgical site. As a result, the surgeon must take additional time to drill the screw to the desired depth; otherwise, the screw will be loose. When the screw is loosely drilled at the surgical site, the screw may pull from the drilling location and cause additional trauma to the patient, requiring further repair and/or surgery.

There have been attempts to provide a better grip for the driver, including altering the size of the handle. As shown in FIGS. 17-18, or example, the handle of a certain conventional driver is oversized to provide additional surface area for gripping the driver. However, the oversized handles are fixed to the driver shaft. Thus, the driver shaft is at a fixed angle relative to the handle. Therefore, the driver shaft can be difficult to manipulate for certain surgical sites and drilling locations. In addition, the driver shaft has a driving end that is fixed and cannot be interchanged to drill a variety of different types of fasteners. Further, as the driver shaft is fixed to the handle, components of traditional drivers cannot be reused or disposed.

Therefore, there is a need for a driver for providing additional torque at multiple angles with a variety of fasteners.

SUMMARY OF THE INVENTION

The present disclosure is directed to embodiments of driver assembly with a rotatable and interchangeable cannulated driver shaft for drilling a variety of fasteners. The driver assembly can include an elongated body having a proximal end and a distal end with a first channel extending from the distal end into the elongated body and a second channel extending from a first side of the elongated body into the elongated body. The driver assembly can also include a locking mechanism connected within the elongated body. The locking mechanism is rotatable between a first configuration and a second configuration. A cannulated driver shaft is removably attached to the locking mechanism and is rotatable between the first configuration and the second configuration via the locking mechanism.

According to another aspect, the driver assembly can include an elongated body having a proximal end and a distal end. A first channel extends from the distal end into the elongated body and a second channel extends from a side of the elongated body into the elongated body. The first channel and the second channel converge at a recess in the elongated body. The driver assembly can also include a cannulated hub rotatably connected to the elongated body in the recess. The cannulated hub is rotatable between a first configuration and a second configuration and a locking mechanism integrated therewith. A cannulated driver shaft is removably attached to the locking mechanism and is rotatable between the first configuration and the second configuration via the locking mechanism.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
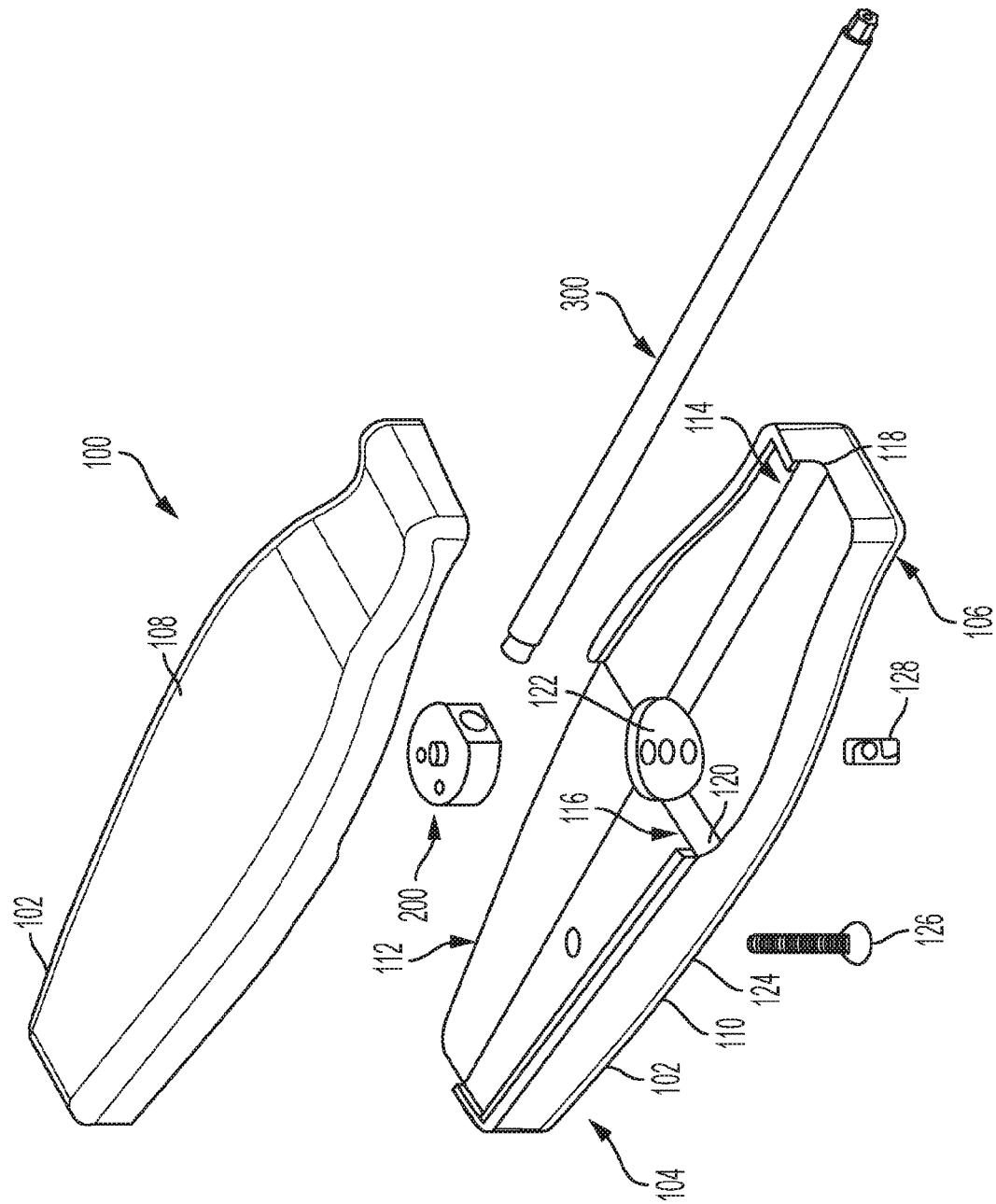
FIG. 1 is an exploded view schematic representation of a driver assembly, according to an embodiment.

Referring now to the figures, wherein like reference numerals refer to like parts throughout, FIG. 1 shows an exploded view schematic representation of a driver assembly 100. In the depicted embodiment, the driver assembly 100 comprises an elongated body 102 extending between a proximal end 104 and a distal end 106. The elongated body 102 and any of other component parts of the driver assembly 100 can be composed of disposable or reusable material. Further, the driver assembly 100 can be manufactured or otherwise assembled to prevent or allow disassembly. The elongated body 102 can be ergonomically designed to improve the grip of the user on the elongated body 102. In the embodiment shown in FIG. 1, the elongated body 102 comprises a first piece 108 and a second piece 110 both sized and configured to align and connect, forming an inner volume 112 of the elongated body 102.

Still referring to FIG. 1, the second piece 110 of the elongated body 102 comprises a first channel 114 and a second channel 116 extending partially therethrough. The first and second channels 114, 116 extend from separate exit points 118, 120 along the elongated body 102 and converge at a central recess 122 in the second piece 110, as shown. In the depicted embodiment, the first channel 114 extends from an exit point 118 at the distal end 106 of the second piece 110 and the second channel 116 extends from an exit point 120 on a first side 124 of the elongated body 102 between the proximal and distal ends 104, 106. In the embodiment shown in FIG. 1, the first channel 114 extends perpendicular to the second channel 116. However, other angular relationships between the first channel 114 and the second channel 116 can be implemented in the elongated body 102 (as should be understood by a person of ordinary skill in the art in conjunction with a review of this disclosure).

As shown in FIG. 1, one or more connectors 126, such as screws or dowel pins, are used to connect the first piece 108 and the second piece 110 of the elongated body 102 as well as other components of the driver assembly 100. A cannulated hub 200 is sized or otherwise configured to fit into the recess 122 within the second piece 110, and is configured to rotate a driver shaft 300. The cannulated hub 200 is rotatable within the recess 122 via a locking mechanism 128. The locking mechanism 128 can be used to hold the driver shaft 300 in the first configuration and the second configuration with a predetermined force that can be overcome with relatively low force (automatic spring action, or manual user actuation) to allow the driver shaft 300 to rotate about the cannulated hub 200. In the depicted embodiment, the locking mechanism 128 is a spring-loaded detent; however alternative similar connectors may be used.

Figure 2:
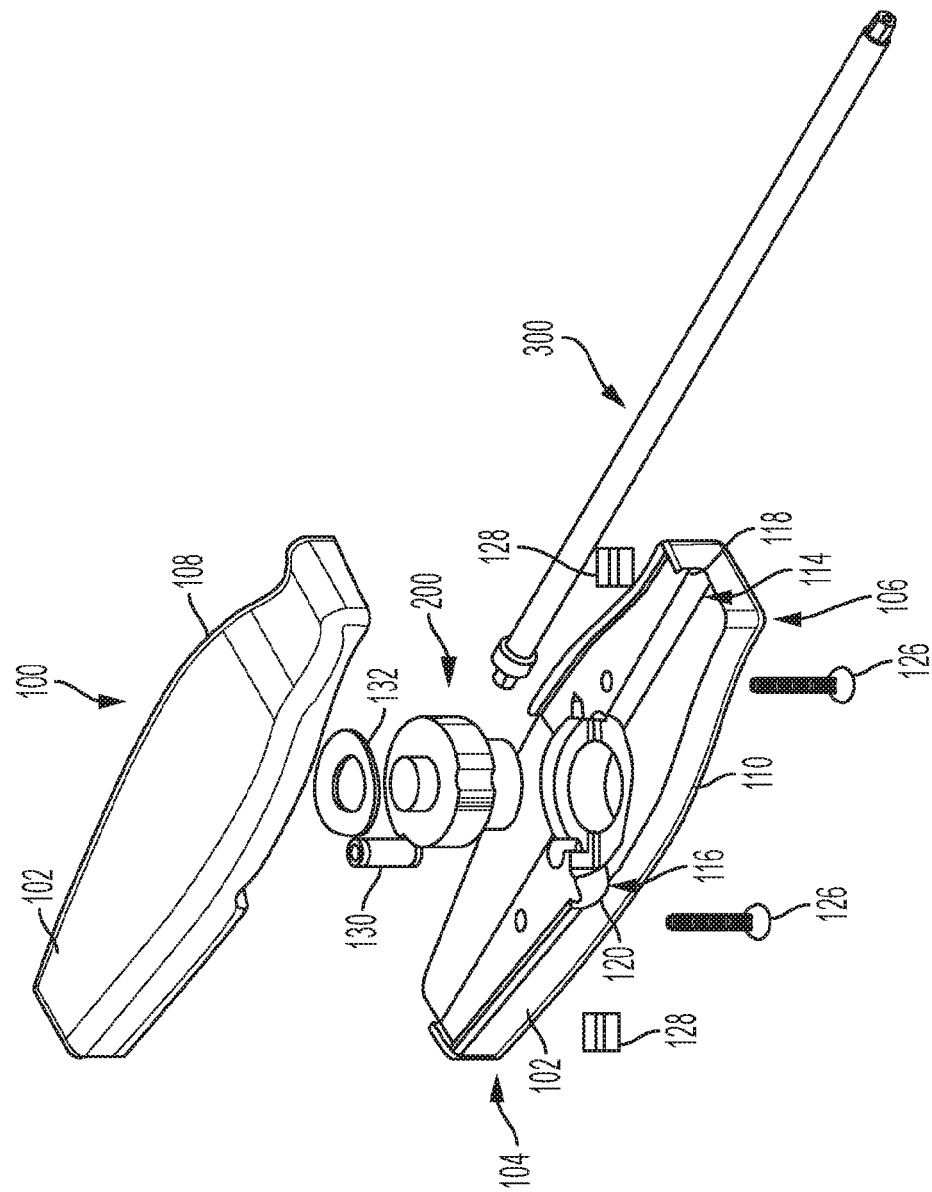
FIG. 2 is an exploded view schematic representation of a driver assembly, according to an alternative embodiment.

An alternative embodiment of the driver assembly 100 is shown in FIG. 2. In the embodiment shown in FIG. 2, the locking mechanism 128 can be one or more keys to be inserted into slots, a spring-loaded detent, or other known locking devices. In FIG. 2, the cannulated hub 200 is held in the first or second configuration by a spring assembly 130/132, such as a wave spring, for example. A key stock 128 locks the cannulated hub 200 in the first or second configuration.

Figure 3:
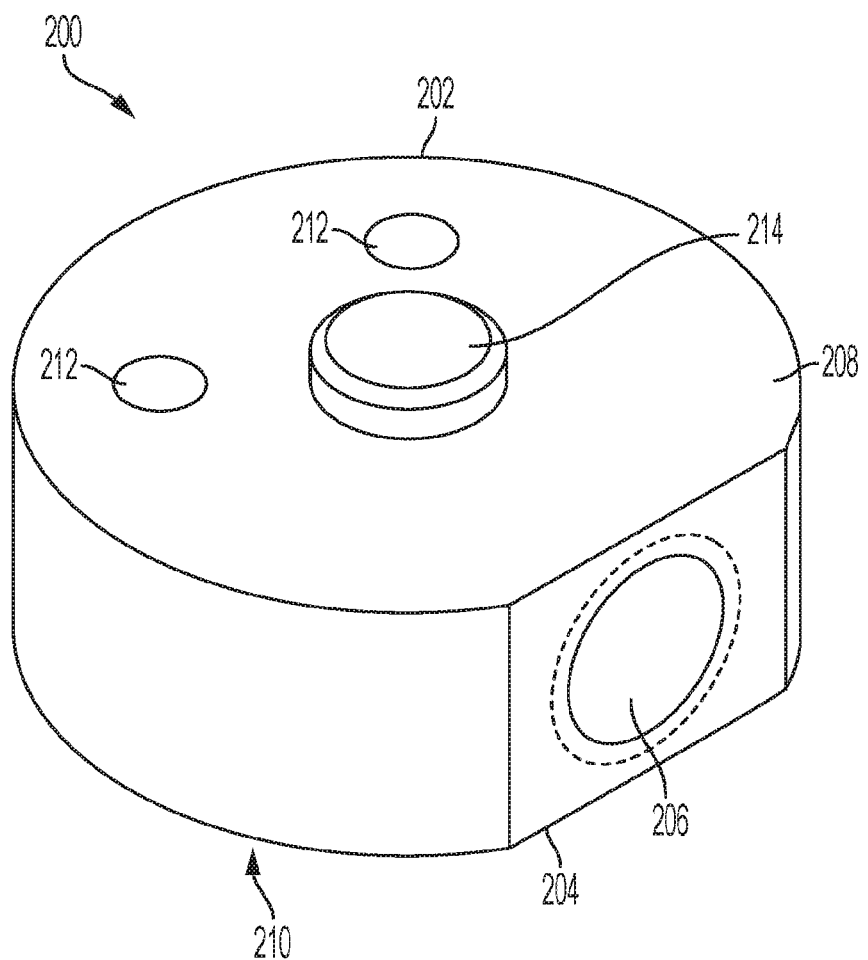
FIG. 3 is a close-up view schematic representation of a cannulated hub, according to an embodiment.

Turning now to FIG. 3, there is shown a close-up perspective view schematic representation of a cannulated hub 200, according to an embodiment. In the depicted embodiment, the cannulated hub 200 has a circular side 202 and one flat side 204. The flat side 204 comprises a threaded aperture 206 extending at least partially through the cannulated hub 200. The threaded aperture 206 is sized or otherwise configured to receive the driver shaft 300 (FIG. 1). The cannulated hub 200 has a first surface 208 and a second surface 210 with the circular side 202 and the flat side 204 extending therebetween. The first surface 208 comprises one or more detent features 212. In the depicted embodiment, the first surface 208 comprises two detent features 212. The detent features 212 are located on the first surface 208 such that they correspond to the threaded aperture 206 aligned with the first channel 114 and the second channel 116. In other words, the location of the detent features 212 on the first surface 208 of the cannulated hub 200 depend on the desired configurations of the driver shaft 300 and the positioning of the first and second channels 114, 116 (e.g., the first channel 114 extends at 90 degrees from the second channel 116). Both the first surface 208 and the second surface 210 of the cannulated hub 200 also comprise one or more central features 214 extending therefrom. The central features 214 interact with the first piece 108 and second piece 110, respectively, of the elongated body 102. The interactions between the central features 214 and the first and second pieces 108, 110 of the elongated body 102 allow the driver shaft 300 to rotate about the axis of the central features 214.

Figure 4:
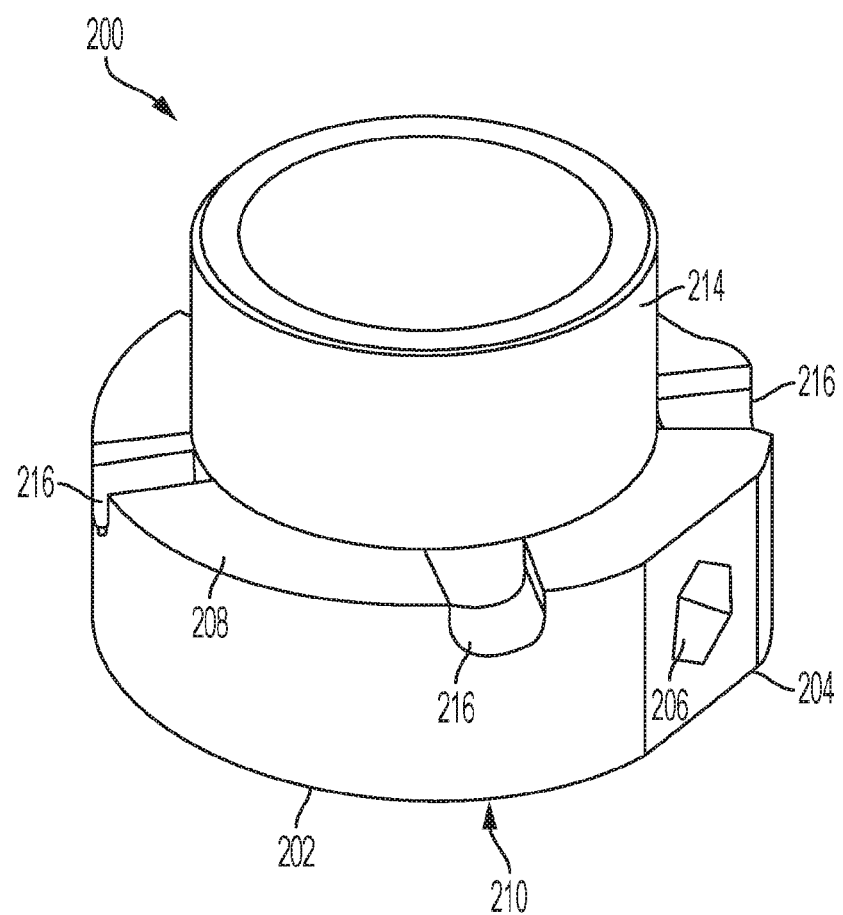
FIG. 4 is a close-up view schematic representation of a cannulated hub, according to an alternative embodiment.
Figure 6:
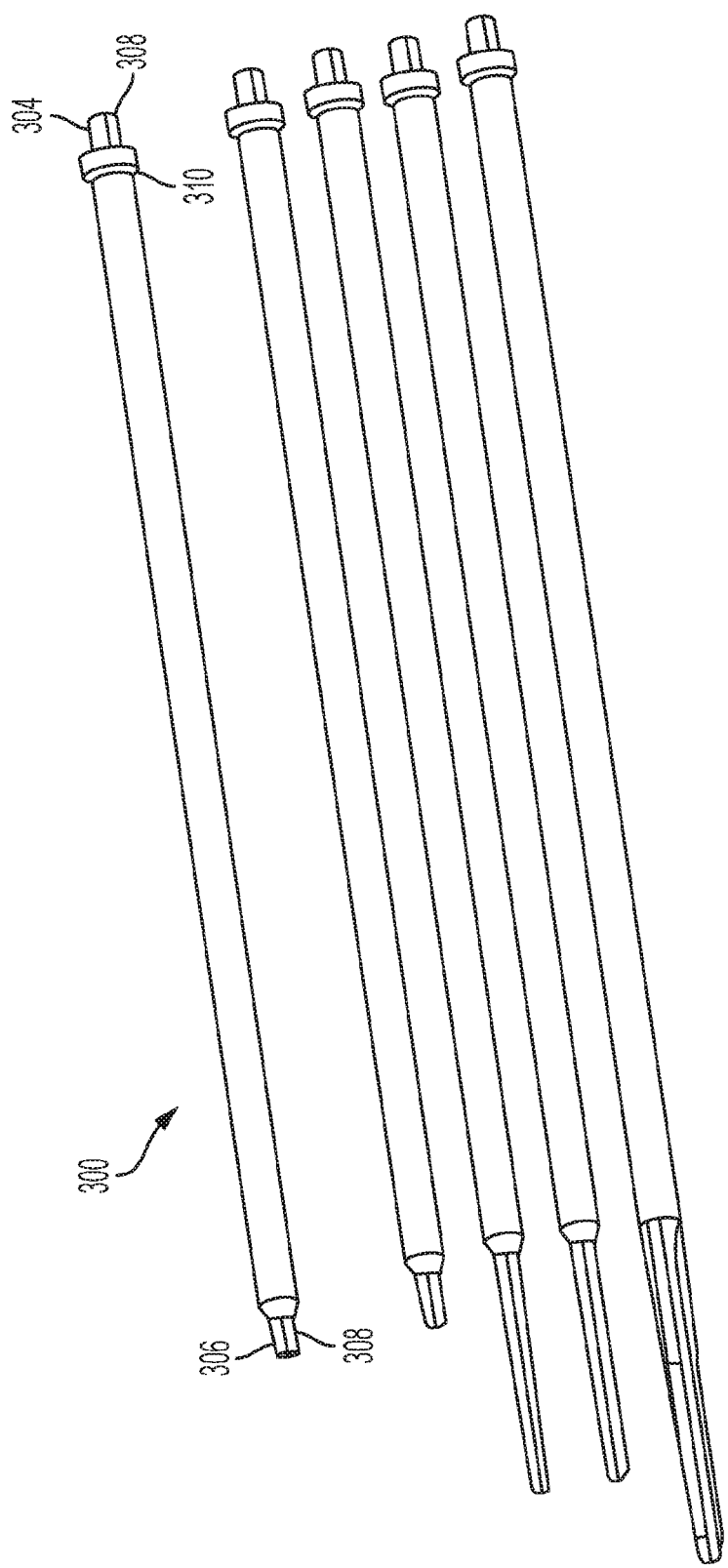
FIG. 6 is a perspective view schematic representation of a variety of driver shafts, according an alternative embodiment.

An alternative embodiment of the cannulated hub 200 is shown in FIG. 4. The cannulated hub 200 in FIG. 4 also has a first surface 208 and a second surface 210 with a circular side 202 and one flat side 204 extending therebetween. However, in the embodiment shown in FIG. 4, the aperture 206 extending at least partially through the flat side 204 of the cannulated hub 200 is a geometric aperture 206. The geometric aperture 206 is shaped, sized, or otherwise configured to receive a driver geometry 308 at a locking end 304 of a driver shaft 300 (FIG. 6). The cannulated hub 200 in FIG. 4 also has a first surface 208 and a second surface 210 with a circular side 202 and one flat side 204 extending therebetween. As shown, the first surface has one or more slot features 216 extending from the circular side 202 through at least a portion of the first surface 208. The slot features 216 lock the driver shaft 300 in the first and second configurations. The slot features 216 extend through the first surface 208 up to the central feature 214. In the depicted embodiment, there are four slot features 216. The number of slot features 216 can vary based on a number of factors, such as the relative positioning of the first and second channels 114, 116 and the desired degree of rotation of the driver shaft 300. In addition, the location of the slot features 216 on the first surface 208 of the cannulated hub 200 depend on the desired configurations of the driver shaft 300 and the positioning of the first and second channels 114, 116 (e.g., the first channel 114 extends at 90 degrees from the second channel 116).

Figure 5:
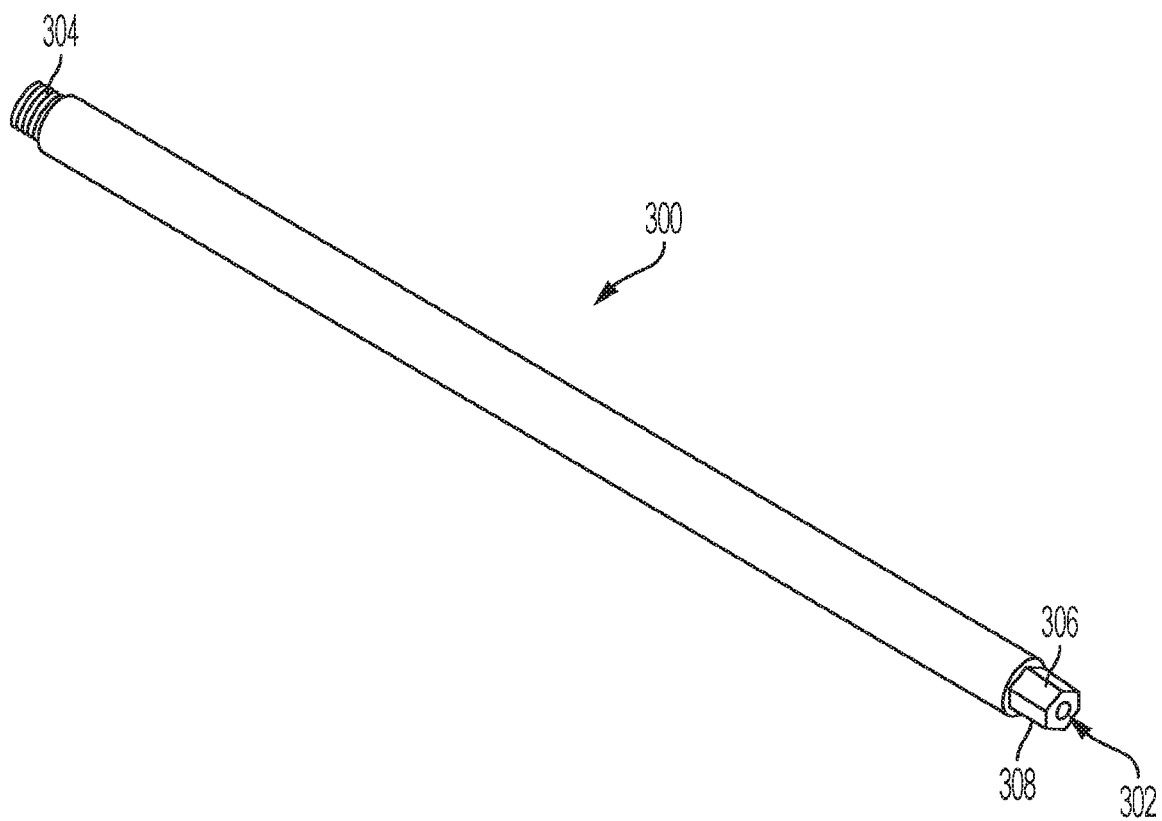
FIG. 5 is a perspective view schematic representation of a driver shaft, according to an embodiment.

Referring briefly to FIG. 5, there is shown a perspective view schematic representation of a driver shaft 300, according to an embodiment. In the depicted embodiment, the driver shaft 300 is a cannulated driver shaft 300 (i.e. with a lumen 302 extending therethrough). The driver shaft 300 has a threaded locking end 304 which is configured to mate with or otherwise engage with the threaded aperture 206 (FIG. 3) to secure the driver shaft 300 within the cannulated hub 200. The driver shaft 300 in FIG. 5 also has an opposing driving end 306. As shown, the driving end 306 has a driver geometry 308 to transmit torque. The driver geometry 308 can be hex, torque, or any other geometry required to properly transmit torque to a fastener (e.g., screw).

In an alternative embodiment of the driver shaft 300 shown in FIG. 6, the driver shaft 300 comprises driver geometry 308 at the locking end 304 to mate or otherwise engage with the geometric aperture 206 on the flat side 204 of the cannulated hub 200. As with the embodiment described above and shown in FIG. 5, the driver shaft 300 of FIG. 6 includes the driver geometry 308 at the driving end 306. The driver geometry 308, at the locking end 304 and the driving end 306, can be hex, torque, or any other geometry required to properly transmit torque to a fastener (e.g., screw). Also in the embodiment of FIG. 6, the driver shaft 300 can include a driver locking feature 310, which locks into the elongated body 102. In the depicted embodiment, the driver locking feature 310 is a ring extending around the driver shaft 300 and abutting the locking end 304 of the driver shaft 300. The driver shaft 300 locks into the elongated body 102 in each of the first and second configurations. The elongated body 102 allows for the driver shafts 300 to be interchanged when the cannulated hub 200 is rotated from the first configuration to the second configuration.

Figure 7A:
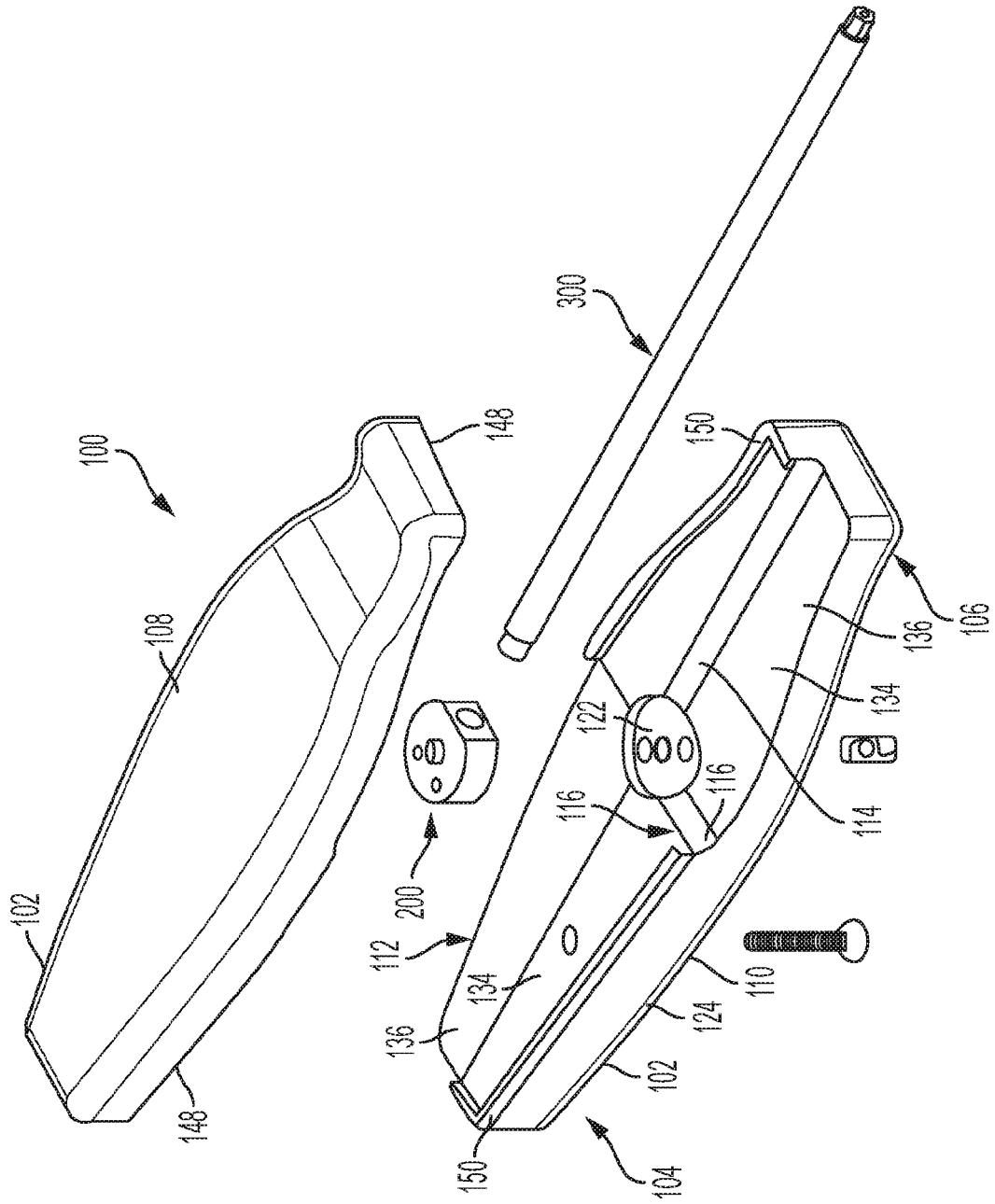
FIG. 7A is an exploded view schematic representation of a driver assembly with a relief area, according to an embodiment.
Figure 7B:
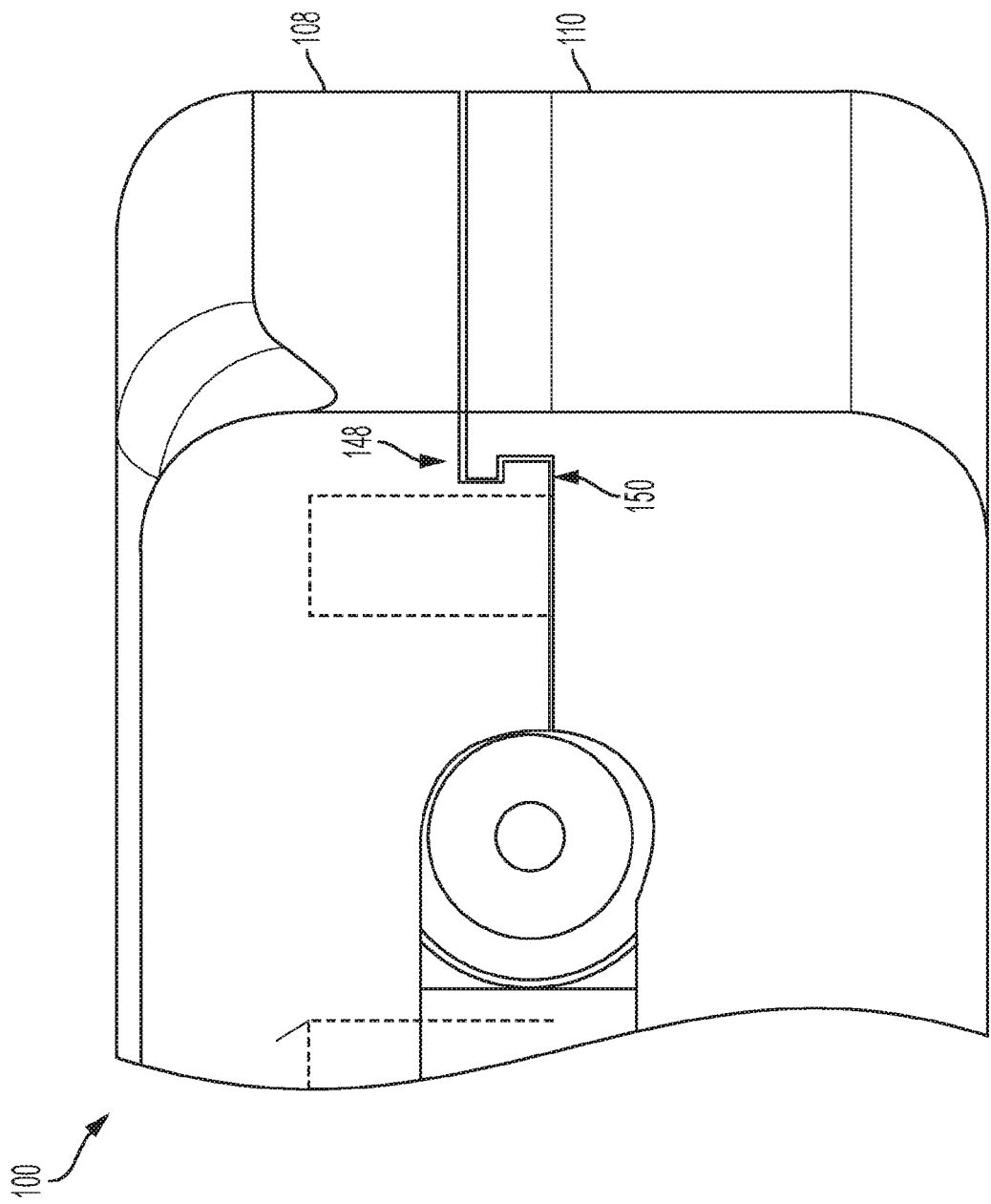
FIG. 7B is a close-up view schematic representation of interfacing flanges on the first and second pieces of the driver assembly, according to an embodiment.

Turning to FIG. 7A, there is shown another exploded view schematic representation of the driver assembly 100, according to an embodiment. In the depicted embodiment, the elongated body 102 comprises one or more relief areas 134 for a guide pin (not shown) and the driver shaft 300. The relief areas 134 provide an uninterrupted space for the guide pin as the driver shaft 300 rotates between the first channel 114 and the second channel 116. In the depicted embodiment, a relief area 134 (a quadrant stepped down from at least one other quadrant, where the channels 114, 116 are further stepped down) is on an inner surface 136 of the second piece 110. The first and second pieces 108, 110 each comprise a flange (or lip) 148, 150, wherein the flanges 148, 150 are configured to align and lock together, as shown in FIG. 7B, overcoming the spring force of the cannulated hub 200 while the driver assembly 100 is fastened together during manufacturing. The interfacing flanges 148, 150 also prevent the first and second pieces 108, 110 from breaking apart or otherwise separating when the driver shaft 300 rotates between the first and second channels 114, 116. The flanges 148, 150 also simplify manufacturing by reducing the number of fasteners of the driver assembly 100.

Figure 8:
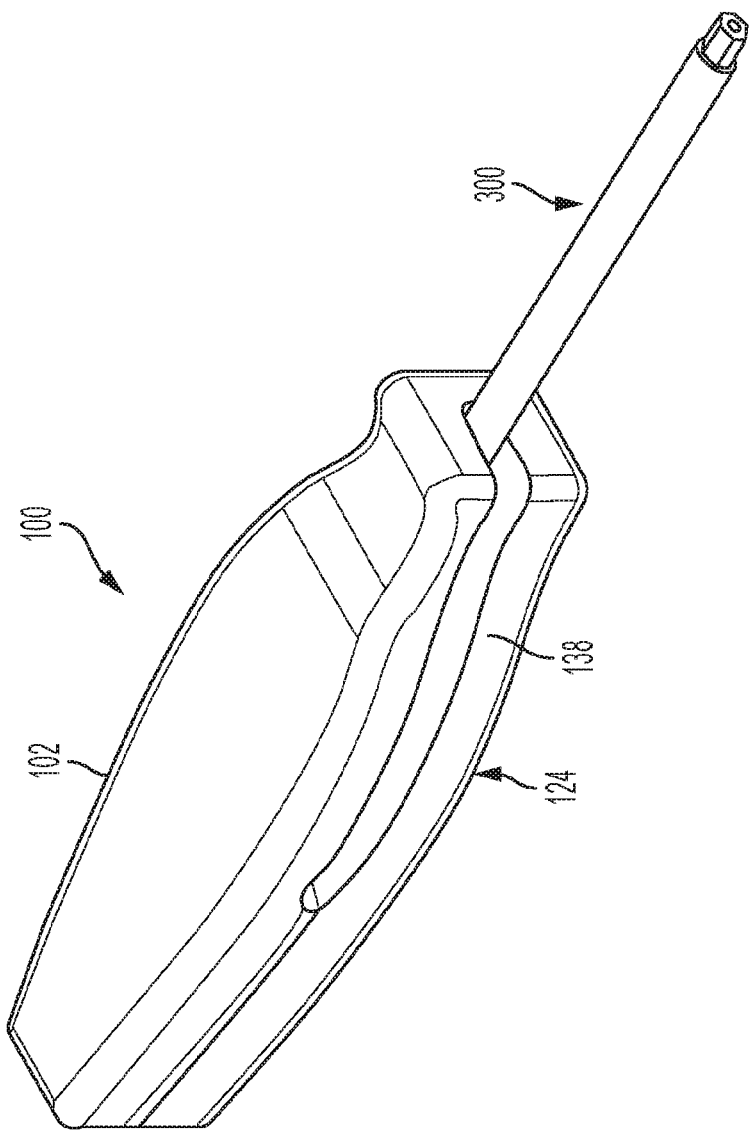
FIG. 8 is a perspective view schematic representation of a driver assembly in the first configuration, according to an embodiment.
Figure 9:
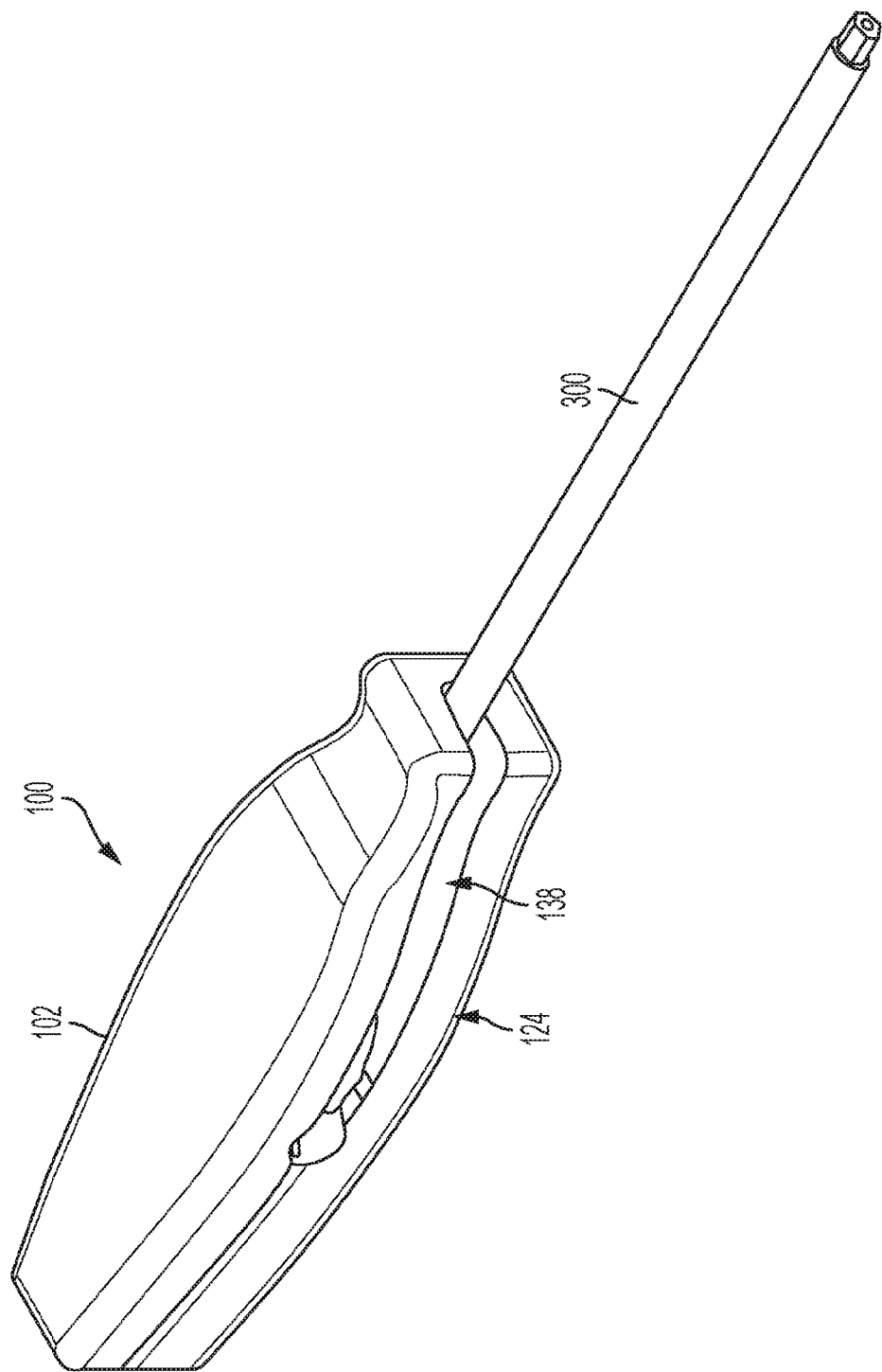
FIG. 9 is a perspective view schematic representation of a driver assembly in the first configuration, according to an alternative embodiment.
Figure 10:
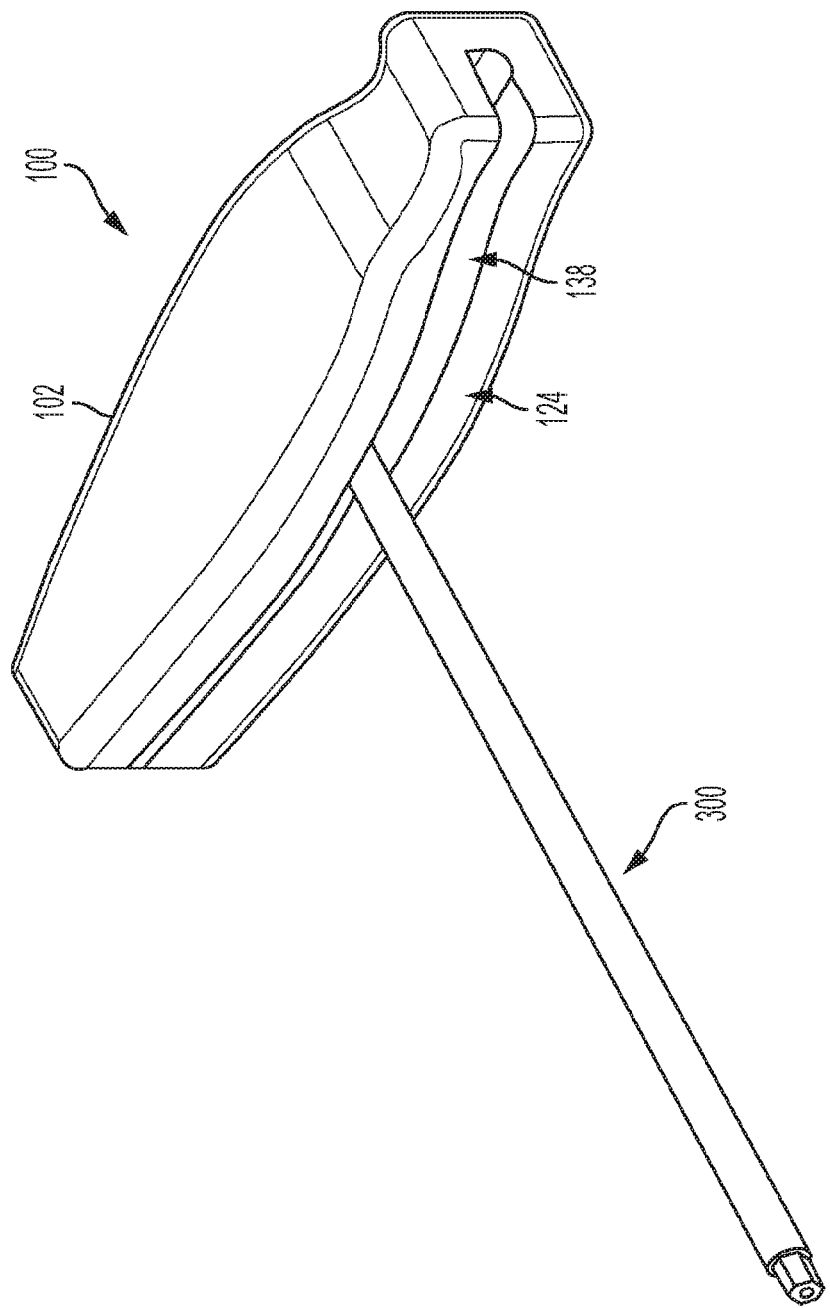
FIG. 10 is a perspective view schematic representation of a driver assembly in the second configuration, according to an embodiment.
Figure 11:
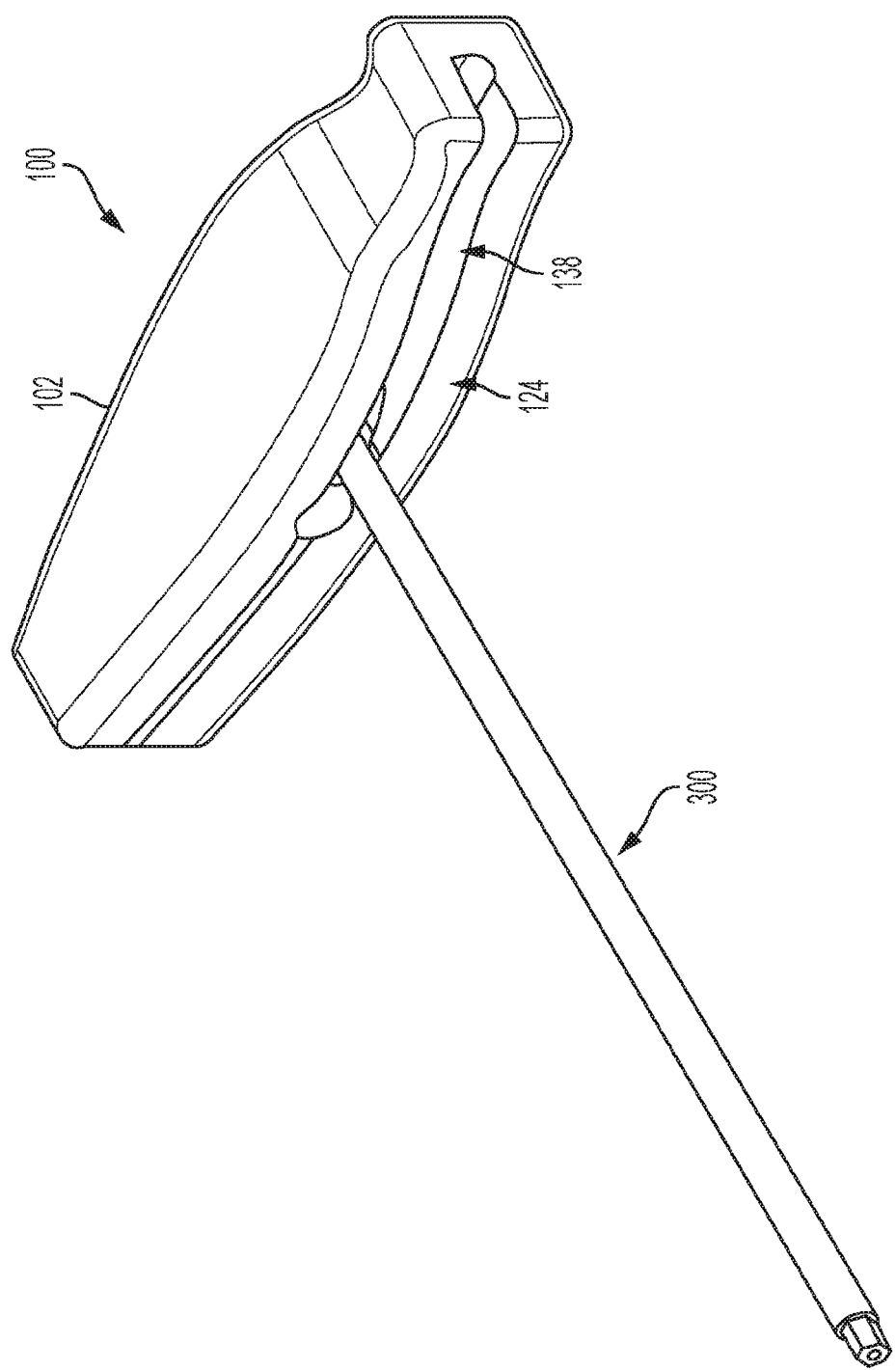
FIG. 11 is a perspective view schematic representation of a driver assembly in the second configuration, according to an alternative embodiment.

Referring now to FIGS. 8-9 and 10-11, there are shown perspective views schematic representations of the driver assembly 100 in the fully assembled first configuration and the second configuration, respectively, according to embodiments. As shown in FIGS. 8-9, in the first configuration, the driver shaft 300 extends through the first channel 114 in the elongated body 102 and out through the distal end 106 of the elongated body 102. The driver shaft 300 is then rotated via the cannulated hub 200 through a first slot 138 (or other space) in the first side 124 of the elongated body 102 between the first piece 108 and second piece 110 to the second channel 116 in order to achieve the second configuration. FIGS. 10-11 show the driver shaft 300 extending through the second channel 116 in the elongated body 102 and out through the first side 124 of the elongated body 102. In embodiments depicted in FIGS. 8-11, the driver shaft 300 rotates 90 degrees between the first configuration (FIGS. 8-9) and the second configuration (FIGS. 10-11).

Figure 12:
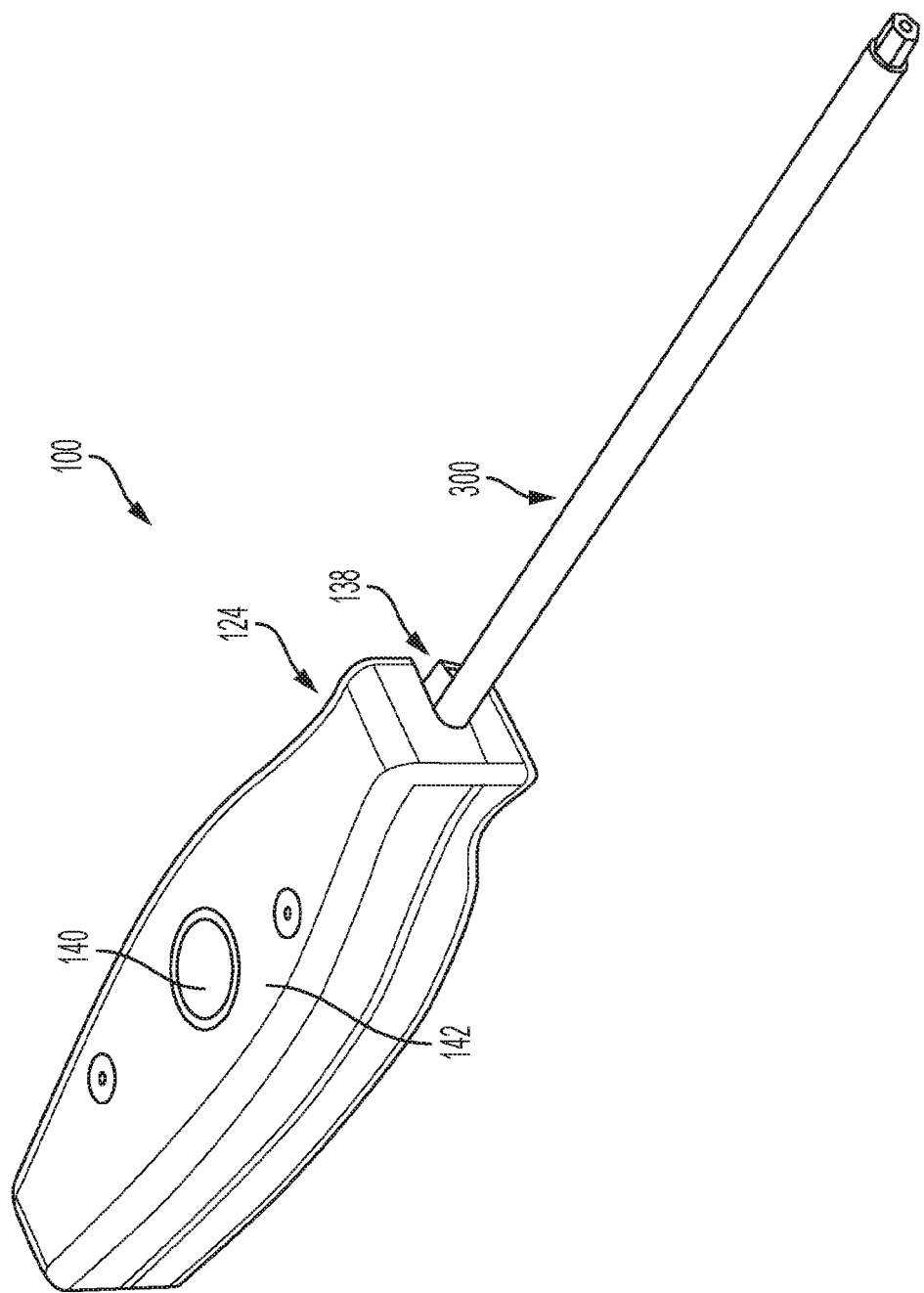
FIG. 12 is a perspective view schematic representation of a driver assembly with an actuator, according to an alternative embodiment.

An alternative embodiment of the driver assembly 100 in the first configuration is shown in FIG. 12. The elongated body 102 comprises an actuator 140 for rotating the driver shaft 300. In the depicted embodiment, the actuator 140 is a button on an outer surface 142 of the first piece 108 of the elongated body 102. By engaging the button 140, the spring assembly 130/132 (coupled thereto) holding the cannulated hub 200 in either the first or second configuration is depressed to allow for rotation (automatic via a biasing member/spring, or via manual actuation) of the driver shaft 300 between the first and second configuration.

Figure 13:
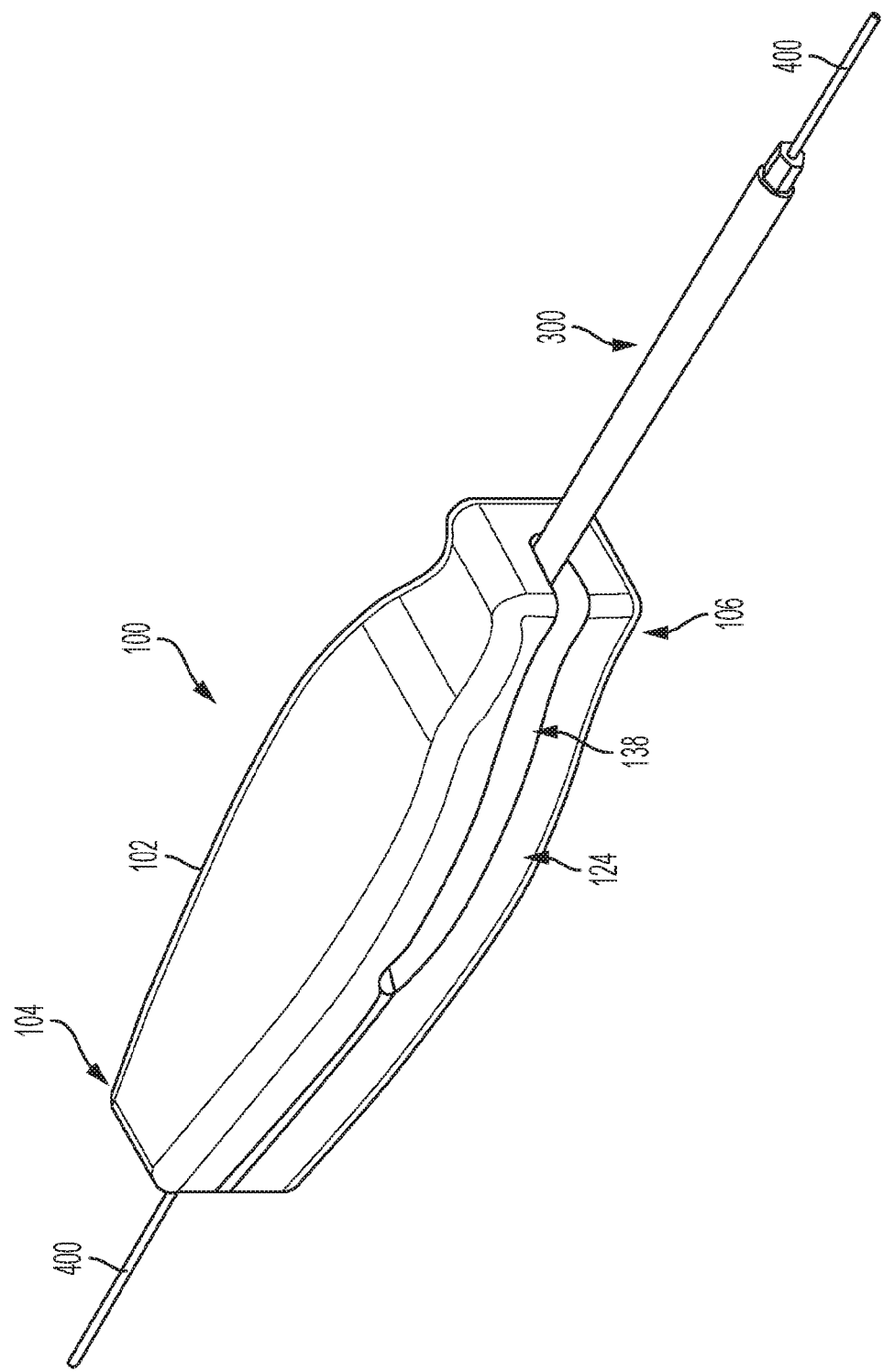
FIG. 13 is a perspective view schematic representation of a driver assembly in the first configuration with a guide pin extending therethrough, according to an embodiment.
Figure 14:
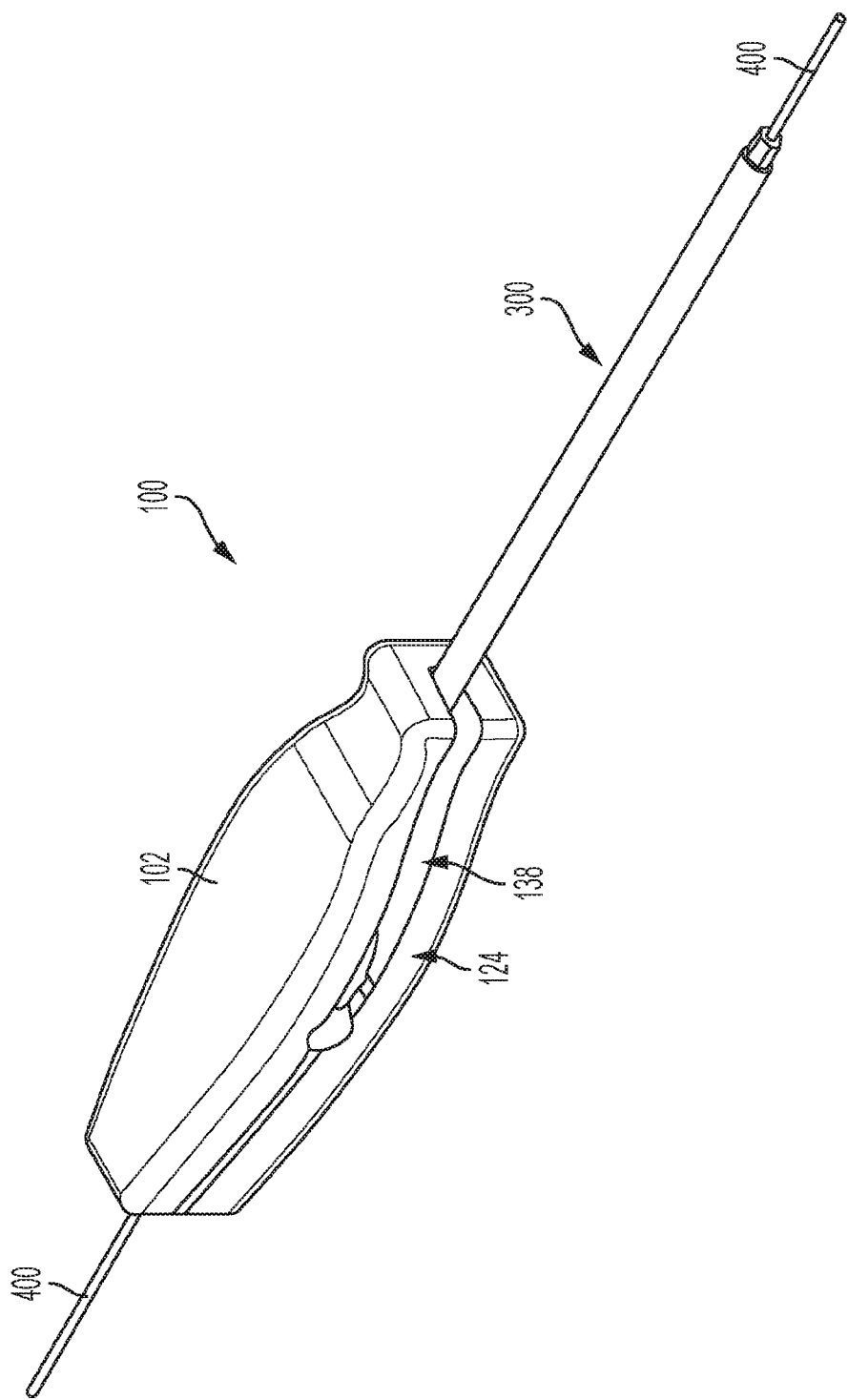
FIG. 14 is a perspective view schematic representation of a driver assembly in the first configuration with a guide pin extending therethrough, according to an alternative embodiment.
Figure 15:
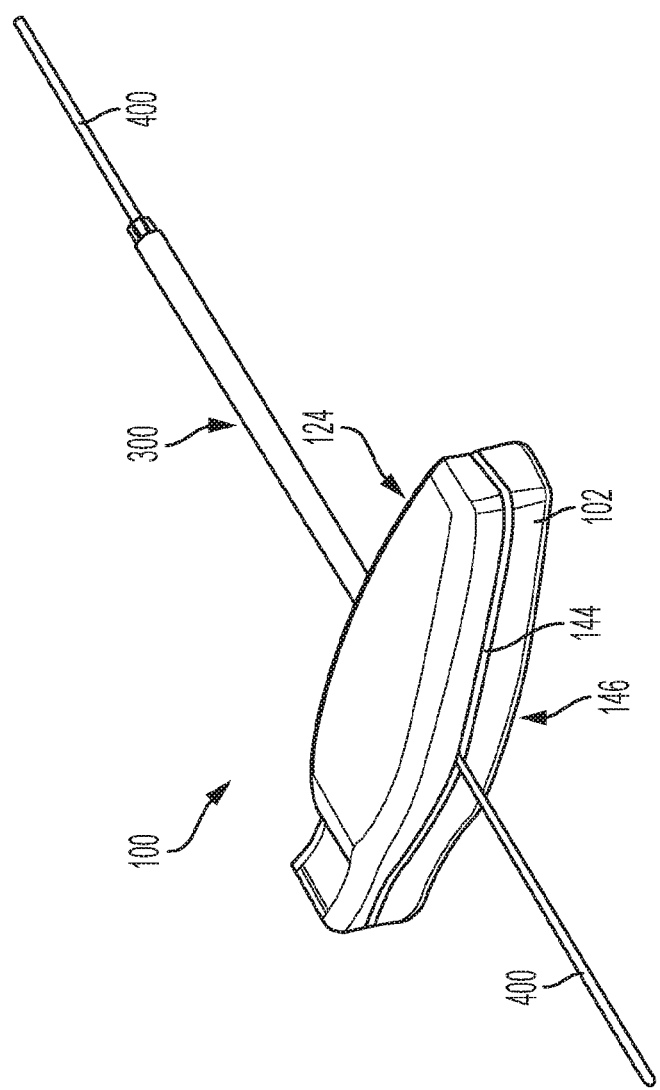
FIG. 15 is a perspective view schematic representation of a driver assembly in the second configuration with a guide pin extending therethrough, according to an embodiment.
Figure 16:
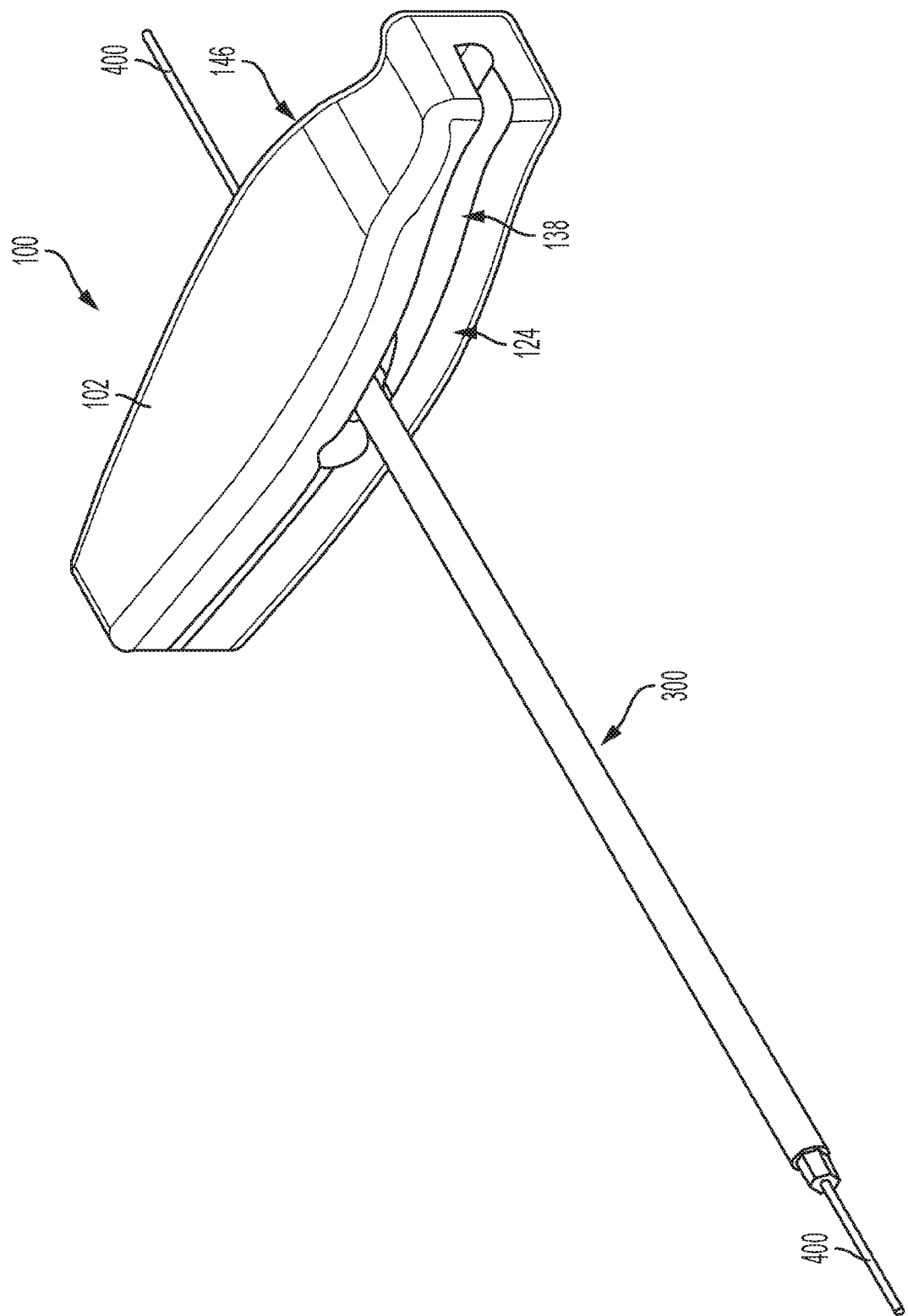
FIG. 16 is a perspective view schematic representation of a driver assembly in the second configuration with a guide pin extending therethrough, according to an alternative embodiment.
Figure 17:
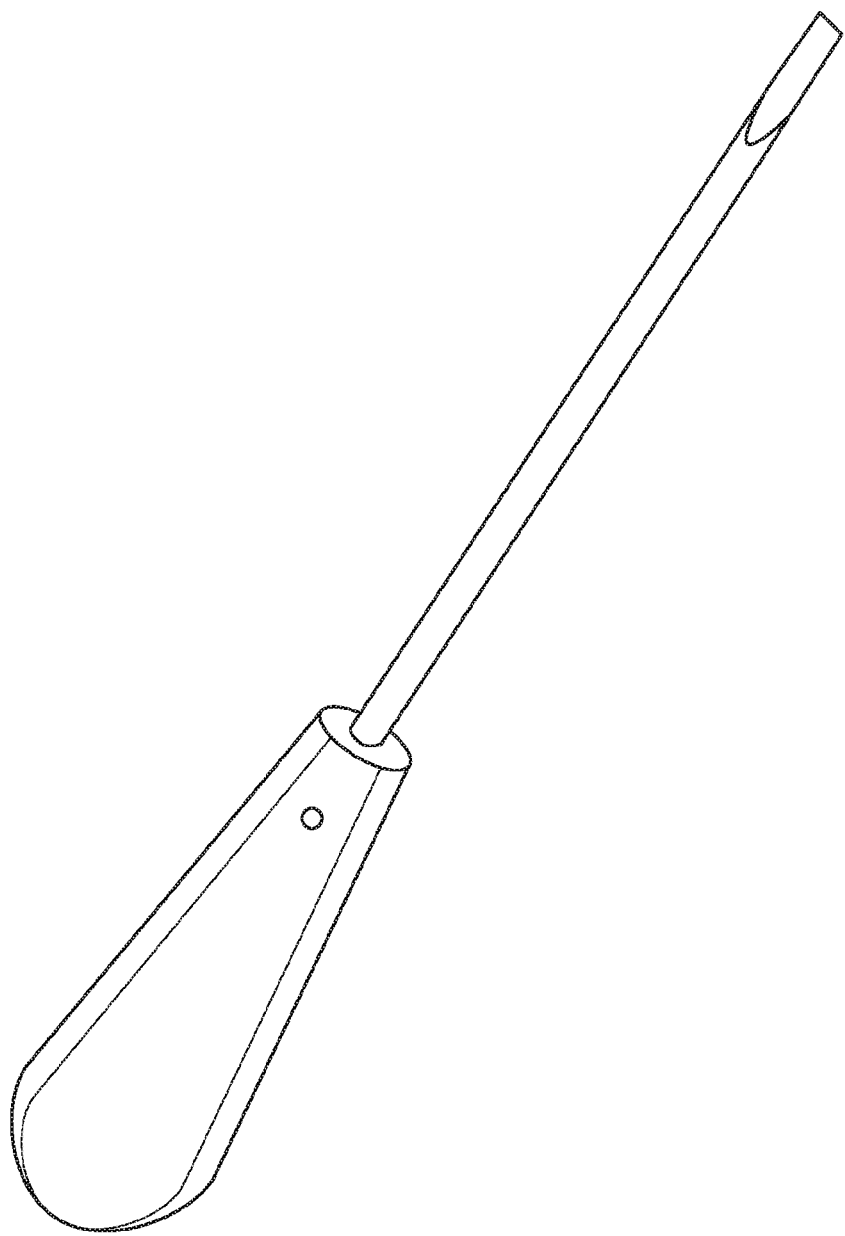
FIG. 17 is a perspective view of a driver of the prior art.
Figure 18:
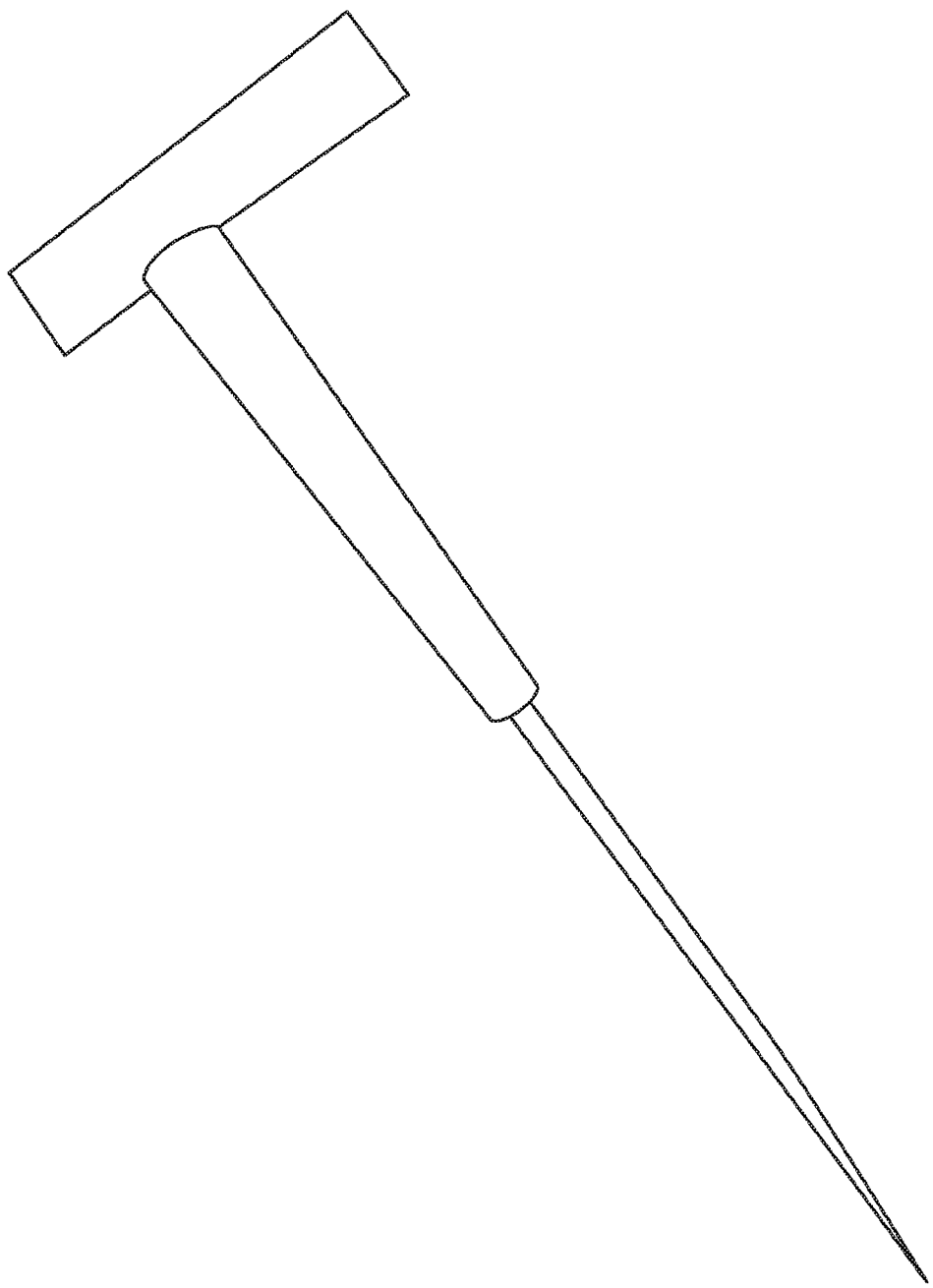
FIG. 18 is a perspective view of another driver of the prior art.

Turning to FIGS. 13-14 and 15-16, there are shown perspective views schematic representations of the driver assembly 100 in the first configuration and the second configuration, respectively, with a guide pin 400 inserted therethrough, according to embodiments. As shown in FIGS. 13-14, in the first configuration, a guide pin 400 is inserted through the proximal end 104 of the elongated body 102 and into the lumen 302 of the cannulated driver shaft 300. As the driver shaft 300 extends through the first channel 114 and out through the distal end 106 of the elongated body 102 in the first configuration, the guide pin 400 also extends out of the distal end 106 of the elongated body 102. The driver shaft 300 and guide pin 400 are then rotated via the cannulated hub 200 to achieve the second configuration shown in FIGS. 15-16. Upon rotation of the driver shaft 300 through the first slot 138, the guide pin 400 rotates through a second slot 144 between the first piece 108 and second piece 110 of the elongated body 102 on a second side 146 of the elongated body 102. FIGS. 15-16 shows the guide pin 400 extending through the second slot 144 on the second side 146 of the elongated body 102 through the driver shaft 300 (in the second channel 116) and out through the first side 124 of the elongated body 102. In embodiment depicted in FIGS. 13-16, the driver shaft 300 and guide pin 400 rotate 90 degrees between the first configuration (FIGS. 13-14) and the second configuration (FIGS. 15-16).

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A driver assembly, comprising:
    an elongated body having a proximal end and a distal end;
    a first channel extending from the distal end into the elongated body;
    a second channel extending from a first side of the elongated body into the elongated body;
    a locking mechanism connected within the elongated body, the locking mechanism rotatable between a first configuration and a second configuration;
    a cannulated driver shaft removably attached to the locking mechanism and rotatable between the first configuration and the second configuration via the locking mechanism.

2. The driver assembly of claim 1, wherein the first channel is substantially perpendicular to the second channel.

3. The driver assembly of claim 1, further comprising a recess within the elongated body wherein the first channel and the second channel converge.

4. The driver assembly of claim 3, wherein the locking mechanism is a cannulated hub rotatably connected to the elongated body within the recess.

5. The driver assembly of claim 4, further comprising a slot and key assembly integrated into the cannulated hub.

6. The driver assembly of claim 4, wherein the cannulated hub has an aperture with a driver geometry.

7. The driver assembly of claim 6, wherein the cannulated driver shaft has a locking end with a driver geometry configured to mate with the driver geometry of the aperture of the cannulated hub.

8. The driver assembly of claim 7, further comprising a driver locking feature on the cannulated driver shaft.

9. The driver assembly of claim 8, wherein the driver locking feature is a ring around the cannulated driver shaft abutting the locking end.

10. The driver assembly of claim 1, further comprising a first slot extending at least partially through the first side of the elongated body.

11. The driver assembly of claim 1, further comprising a second slot extending at least partially through a second side of the elongated body, wherein the second side opposes the first side.

12. A driver assembly, comprising:
    an elongated body having a proximal end and a distal end;
    a first channel extending from the distal end into the elongated body;
    a second channel extending from a first side of the elongated body into the elongated body;
    wherein the first channel and the second channel converge at a recess in the elongated body;
    a cannulated hub rotatably connected to the elongated body in the recess, the cannulated hub rotatable between a first configuration and a second configuration;
    a locking mechanism integrated with the cannulated hub;
    a cannulated driver shaft removably attached to the locking mechanism and rotatable between the first configuration and the second configuration via the locking mechanism.

13. The driver assembly of claim 12, wherein the first channel is substantially perpendicular to the second channel.

14. The driver assembly of claim 12, wherein the locking mechanism is a spring-loaded detent.

15. The driver assembly of claim 12, wherein the cannulated hub has a threaded aperture configured to mate with a threaded locking end of the cannulated driver shaft.

16. The driver assembly of claim 12, further comprising a first slot extending at least partially through the first side of the elongated body and a second slot extending at least partially through a second side of the elongated body, wherein the second side opposes the first side.

17. The driver assembly of claim 16, further comprising a guide pin extending through a lumen of the cannulated driver shaft.

18. The driver assembly of claim 17, wherein between the first configuration and the second configuration, the guide pin extends through the second slot and the cannulated driver shaft extends through the first slot.

19. The driver assembly of claim 18, wherein between the first and second configurations, the guide pin and the cannulated driver shaft extend through relief areas in the elongated body.

20. The driver assembly of claim 12, further comprising an actuator on an outer surface of the elongated body operably connected to the locking mechanism.

* * * * *